(12) United States Patent
Fanslow, III et al.

(10) Patent No.: US 7,833,697 B2
(45) Date of Patent: Nov. 16, 2010

(54) ENDOTHELIAL STEM CELLS, POPULATIONS, METHODS OF ISOLATION AND USE THEREOF

(75) Inventors: William C. Fanslow, III, Seattle, WA (US); Anne-Marie C. Rousseau, Seattle, WA (US); Thomas O. Daniel, Seattle, WA (US)

(73) Assignee: Immunex Corporation, Thousand Oaks, CA (US)

( * ) Notice: Subject to any disclaimer, the term of this patent is extended or adjusted under 35 U.S.C. 154(b) by 716 days.

(21) Appl. No.: 10/327,322

(22) Filed: Dec. 20, 2002

(65) Prior Publication Data

US 2003/0148512 A1  Aug. 7, 2003

Related U.S. Application Data

(60) Provisional application No. 60/343,498, filed on Dec. 21, 2001.

(51) Int. Cl.
*A01N 1/02* (2006.01)
*C12N 15/86* (2006.01)

(52) U.S. Cl. .......................... 435/2; 435/325

(58) Field of Classification Search ........................ None
See application file for complete search history.

(56) References Cited

U.S. PATENT DOCUMENTS

| 5,980,887 | A | 11/1999 | Isner et al. | |
|---|---|---|---|---|
| 6,623,940 | B1 * | 9/2003 | Ledbetter et al. | ........... 435/69.1 |
| 6,852,537 | B2 * | 2/2005 | Hebbel et al. | ................ 435/402 |

FOREIGN PATENT DOCUMENTS

| JP | 2005-514062 | 5/2005 |
|---|---|---|
| WO | WO 98/19712 | 5/1998 |
| WO | WO99/37751 | 7/1999 |
| WO | WO01/94420 | 12/2001 |
| WO | WO 03/060077 A | 7/2003 |

OTHER PUBLICATIONS

Mandel et al, Blood Nov. 2001;98(11-part2):55.*
Schweitzer et al, Exp Hematol 1995;23:41-8.*
Watt et al, Blood 2000;95:3113-24.*
Clancy et al., Arthrit Rheumat 2001;44 :1203-8.*
Solovey et al, NEJM 1997;337:1584-90.*
Gupta et al, Exp Cell Res 1997;230:244.*
Domotor et al, Neurochem Int. 1998;33(6):473-8.*
Walenta et al. Biochem Biophy Res Comm 2005;333:476-82.*
Delorme et al. Thromb Haemost 2005;94:1270-9.*
Martin-Padura et al. Curr Pharm Design 2008;14:3780-9.*
Bossuyt et al. Cytometry 1997;30:124-33.*
Pulido et al. J Immunol 1998;140:3851-7.*
Strijbos et al. Brit J Cancer 2008;98:1731-5.*
Bhatia et al., "AC133 expression in stem cells," *Leukemia* 15:1685-1688, 2001.
Filshie et al., "MUC18, a member of the immunoglobulin superfamily, is expressed on bone marrow fibroblasts and a subset of hematological malignancies," *Leukemia* 12:414-421, 1998.
Ikpeazu et al., "Donor origin of circulating endothelial progenitors after allogeneic bone marrow transplantation," *Bio Blood Marrow Transplant* 6:301-308, 2000.
Leukocyte Typing VII, Mason et al. (ed.s), Oxford University Press, 2002, pp. 344-346.
Quirici et al., "Differentiation and expansion of endothelial cells from human bone marrow $CD133^+$ cells," *Brit J Haematl* 115:186-194, 2001.
Solovey et al., "Identification and functional assessment of endothelial P1 H12," *J Lab Clin Med* 138 322-331, 2001.
Spangrude et al., "Resting and activated subsets of mouse multipotent hematopoietic stem cells," *Proc Natl Acad Sci USA* 87:7433-7437, 1990.
Wiley et al., "A novel TNF receptor family member binds TWEAK and is implicated in angiogenesis," *Immunity* 15:837-846, 2001.
Woywodt et al., "Detection of circulating endothelial cells," *DYNALogue* 2:20-21, 2003.
International Search Report, PCT/US02/41161, mailed Nov. 12, 2003.
Asahara et al., "Isolation of Putative Progenitor Endothelial Cells for Angiogenesis," *Science* 275:964-967, 1997.
Gehling et al., "In vitro differentiation of endothelial cells from AC133-positive progenitor cells," *Blood* 95 (10):3106-3112, 2000.
Gill et al, "Vascular Trauma Induces Rapid but Transient Mobilization of $VEGFR2^+AC133^+$ Endothelial Precursor Cells," *Circ. Res.* 88:167-174, 2001.
Huss, "Isolation of Primary and Immortalized $CD34^-$ Hematopoietic and Mesenchymal Stem Cells from Various Sources," *Stem Cells* 18:1-9, 2000.
Kalka et al, "Transplantation of ex vivo expanded endothelial progenitor cells for therapeutic neovascularization," *Proc. Natl. Acad. Sci. USA* 97(7):3422-3427, 2000.

(Continued)

*Primary Examiner*—Q. Janice Li
(74) *Attorney, Agent, or Firm*—Nathan A. Machin (57) ABSTRACT

The present invention provides stem cells characterized as having the ability to renew and the ability to give rise to endothelial and/or endothelial-like cells, methods of isolating such stem cells and methods of use thereof. Also provided are progeny cells derived from the stem cells of the invention.

4 Claims, 3 Drawing Sheets

OTHER PUBLICATIONS

Kawamoto et al., "Therapeutic Potential of Ex Vivo Expanded Endothelial Progenitor Cells for Myocardial Ischemia," *Circulation* 103:634-637, 2001.

Peichev et al., "Expression of VEGFR-2 and AC133 by circulating human CD34+ cells identified a population of functional endothelial precursors," *Blood* 95(3):952-958, 2000.

Qun Shi et al., "Evidence for Circulating Bone Marrow-Derived Endothelial Cells," *Blood* 92:362-367, 1998.

St. Croix et al., "Genes Expressed in Human Tumor Endothelium," *Science* 289:1197-1202, 2000.

European Exam Report, Application No. 02796023.6 (PCT/US0241161), Jan. 16, 2006.

Burger P.E., et al., "Fibroblast growth factor receptor-1 is expressed by endothelial progenitor cells," *Blood* 100(10):3527-3535, 2002.

Almeida-Porada G. and Ascensao J. L. "Isolation, characterization, and biologic features of bone marrow endothelial cells," *Journal of Laboratory and Clinical Medicine* 128 (4):399-407,1996.

Ito H., et al., "Endothelial Progenitor Cells as Putative Targets for Angiostatin,"*Cancer Research* 59:5875-5877, 1999.

Gronthos et al. "Surface Protein Characterization of Human Adipose Tissue-Derived Stromal Cells". *J. Cell. Physiol.* 189: 54-63 (20001).

Mehra et al. "Progenitor Marker CD133 mRNA Is Elevatied in Peripheral Blood of Cancer Patients with Bone Metastases." *Clin. Cancer Res.* 12(16):4859-4866 (2006).

Vainlo et al. "HEMCAM, an Adhesion Molecule Expressed by c-Kit Hemopoietic Progenitors" *J. Cell Biol.* 135(6):1655-1668 (1996).

Balconi, G. et al., Arterioscler. Thromb, Vasc. Biol. 2000, 20:1443-1451.

* cited by examiner

ENDOTHELIAL STEM CELLS, POPULATIONS, METHODS OF ISOLATION AND USE THEREOF

This application claims priority to provisional application 60/343,498, filed Dec. 21, 2001.

FIELD OF THE INVENTION

The present invention provides stem cells characterized as having the ability to renew and the ability to give rise to endothelial and/or endothelial-like cells, methods of isolating such stem cells and methods of use thereof. Also provided are progeny cells derived from the stem cells of the invention.

BACKGROUND

The mammalian body is composed of several lineage-committed cells that give rise to the many tissues of a mammalian body. Despite the diversity of the nature, morphology, characteristics and function of such lineage committed cells, it is presently believed that most, if not all, the lineage committed cells are derived from various stem cells that give rise to one or more of the lineage committed cells of the mammalian body. Such stem cells constitute only a small percentage of the total number of cells present in the body and can vary depending up their relative commitment to a particular cell type. In addition, it is not known what markers associated with lineage committed cells are also present on stem cells. One marker which has been indicated as present on stem cells, CD34, is also found on a significant number of lineage committed progenitors. In particular, B-cells (CD19$^+$) and myeloid cells (CD33$^+$) make up 80-90% of the CD34$^+$ population. Moreover, a combination of CD3, 8, 10, 15, 19, 20, and 33 will be present on >90% of all CD34$^+$ cells. Therefore, in view of the small proportion of the total number of cells in the bone marrow which are stem cells, the uncertainty of the markers associated with the stem cell as distinct from more differentiated cells, and the general inability to biologically assay for human stem cells, the identification and purification of stem cells has been elusive.

Endothelial cells are a cellular organizational unit of vascular structures. Their linear commitment, expansion, and assembly into blood vessels are required for organogenesis during embryonic development. During angiogenesis, endothelial cells in existing vessels are activated by angiogenesis factors, such as TGF, FGF, and VEGF. New vessels are formed through cell proliferation and migration, and the elongation and branching of existing vessels.

Identification of a readily available source of stem cells that can give rise to endothelial cells is needed. The need is particularly acute for stem cells from adult sources, in light of restrictions recently placed on the use of federal funding for embryonic stem cell research. Possession of such stem cells will allow for identification of growth factors associated with endothelial cell regeneration. In addition, there may be as yet undiscovered growth factors or other biological factors (e.g., transcription factors) associated with the early steps of dedication of the stem cell to an endothelial cell lineage, the prevention of such dedication, and the negative control of stem cell proliferation. The availability of stem cells would be extremely useful in vascular transplantation, tissue engineering, regulation of angiogenesis, vasculogenesis, and the prevention thereof. The stem cells and their progeny can find use in the treatment of myocardial damage and repair. Such stem cells also could be used to introduce a gene into a subject as part of a gene therapy regimen.

SUMMARY OF THE INVENTION

In one embodiment, the present invention provides a method of preparing an enriched population of stem cells, comprising separating said enriched population of stem cells from a first population of cells, wherein said enriched population of stem cells comprises at least about a 100-fold greater concentration of P1H12+ stem cells than said first population of cells. In another embodiment, said enriched population of stem cells comprises at least about a 1,000-fold greater concentration of P1H12+ stem cells than said first population of cells. In another embodiment, said enriched population of stem cells comprises at from about a 1,000-fold to about a 4,000-fold greater concentration of P1H12+ stem cells than said first population of cells. In another embodiment, said enriched population of stem cells further comprises between a greater concentration than said first population of cells of one or more of the markers selected from the group consisting of CD148, AC133, CD45 and CD34. In another embodiment, said separating step comprises contacting said first population of cells with a molecule that specifically binds to P1H12+ and selecting for said enriched population cells that are bound to said molecule. In another embodiment, said molecule is an antibody. In another embodiment, said antibody is a monoclonal antibody. In another embodiment, said molecule is derived from an antibody. In another embodiment, said molecule is a peptide-Fc fusion molecule. In another embodiment, said separating step further comprises contacting said first population of cells with a molecule that specifically binds to a molecule selected from the group consisting of CD 148, AC 133, CD45 and CD34 and selecting for said enriched population of cells that are bound to said molecule. In another embodiment, said separating step further comprises contacting said enriched population of cells with a molecule that specifically binds to a marker selected from the group consisting of CD148, AC133, CD45 and CD34 and removing from said enriched population of cells cells that are not bound to said molecule. In another embodiment, said separating step further comprises contacting said first population of cells with a molecule that specifically binds to a molecule selected from the group consisting of CD144, CD202b, VEGFR2 and selecting for said enriched population of cells cells that are not bound to said molecule. In another embodiment, said separating step further comprises contacting said enriched population of cells with a molecule that specifically binds to a molecule selected from the group consisting of CD 144, CD202b, VEGFR2 and removing from said enriched population of cells cells that are bound to said molecule. In another embodiment, said enriched population of stem cells comprises at least about a 100-fold greater concentration of stem cells that are P1H12+, CD148+, AC133+, CD 144−, CD202b− or VEGFR2− than said first population of cells. In another embodiment, said enriched population of stem cells comprises at least about a 1,000-fold greater concentration of stem cells that are P1H12+, CD148+, AC133+, CD144−, CD202b− or VEGFR2− than said first population of cells. In another embodiment, said enriched population of stem cells comprises from about a 1,000-fold to about a 4,000-fold greater concentration of stem cells that are P1H12+, CD148+, AC133+, CD144−, CD202b− or VEGFR2− than said first population of cells. In another embodiment, said enriched population of stem cells are further enriched for stem cells that are CD34+ or CD45+. In another embodiment, said enriched population of stem cells are further enriched for stem cells that are CD34− and CD45+. In another embodiment, said enriched population of stem cells are further enriched for stem cells that are CD34+ and CD45+. In another embodiment, said molecule is bound to a detectable entity. In another embodiment, said detectable entity is a fluorescent entity, a colorimetric entity, or a magnetic entity. In another embodiment, said molecule is bound to a solid substrate. In another embodiment, said solid substrate is a plastic surface, a glass surface, agarose, acrylamide, lectin or a magnetic particle. In another embodiment, said method further comprises the step of culturing said enriched population of stem cells to give rise to progeny cells that are P1H12+, CD144+, AC133−, CD202+, CD45−, VEGFR2+, have a higher proliferative capacity than HUVECs and MVECs, and contain Weibel-Palade Bodies. In another embodiment, said first population of cells is derived from a mammal. In another embodiment, said mammal is a primate. In another embodiment, said primate is a human. In another embodiment, said first population of cells is derived from peripheral blood. In another embodiment, said first population of cells is derived from bone marrow. In another embodiment, said first population of cells is derived from fetal liver tissue.

In another embodiment, the present invention provides a population of stem cells prepared as above. In another embodiment, said stem cells are positive for one or more of a marker selected from the group consisting of CD148, AC133, CD45 and CD34. In another embodiment, said enriched population of stem cells is enriched for stem cells that are P1H12+, CD 148+, AC133+, CD 144−, CD202b− and VEGFR2—. In another embodiment, said enriched population of stem cells is further enriched for stem cells that are CD34+ or CD45+. In another embodiment, said enriched population of stem cells is further enriched for stem cells that are CD34+ and CD45+. In another embodiment, said enriched population of stem cells is further enriched for stem cells that are CD34− and CD45+. In another embodiment, said stem cells contain Weibel-Palade Bodies. In another embodiment, said stem cells are endothelial progenitor cells. In another embodiment, said first population of cells is derived from a mammal. In another embodiment, said mammal is a primate. In another embodiment, said primate is a human. In another embodiment, said first population of cells is derived from peripheral blood. In another embodiment, said first population of cells is derived from bone marrow. In another embodiment, said first population of cells is derived from fetal liver tissue.

In another embodiment, the present invention provides a population of progeny cells derived from the enriched population of stem cells, wherein said progeny cells are P1H12+, CD 144+, AC 133−, CD202+, CD45−, VEGFR2+, have a higher proliferative capacity than HUVECs and MVECs, and contain Weibel-Palade Bodies.

In another embodiment, the present invention provides an isolated stem cell that is P1H12+ and AC133+ and that can self-renew and differentiate into an endothelial cell. In another embodiment, the isolated stem cell is further CD 148+, CD 144−, VEGFR2− and CD202b−. In another embodiment, said isolated stem cell is further CD34+ or CD45+. In another embodiment, said isolated stem cell is further CD34+ and CD45+. In another embodiment, said isolated stem cell is further CD34− and CD45+. In another embodiment, said stem cell is derived from a mammal. In another embodiment, said mammal is a primate. In another embodiment, said primate is a human. In another embodiment, said first population of cells is derived from peripheral blood. In another embodiment, said first population of cells is derived from bone marrow. In another embodiment, said first population of cells is derived from fetal liver tissue. In another embodiment, said isolated stem cell is capable of being cultured for at least 14, days in a complete medium comprising 15% serum. In another embodiment, said isolated stem cell further comprises a heterologous polynucleotide sequence.

In another embodiment, the present invention provides a cell line comprising an isolated stem cell as described above or a progeny cell thereof.

In another embodiment, the present invention provides a stem cell culture comprising a substantially homogenous population of stem cells as described above.

In another embodiment, the present invention provides a composition comprising an isolated stem cell as described above and a pharmaceutically acceptable carrier. In another embodiment, said pharmaceutically acceptable carrier is selected from the group consisting of saline, a gel, a hydrogel, a sponge, and a matrix.

In another embodiment, the present invention provides an isolated progeny cell obtained by culturing an isolated stem as described above for about 6 days to about 3 weeks in complete medium with 15% serum, wherein the progeny cell is characterized as being P1H12+, CD 144+, AC 133−, CD202+, CD45−, VEGFR2+, have a higher proliferative capacity than HUVECs and MVECs, and contain Weibel-Palade Bodies.

In another embodiment, the present invention provides a progeny cell culture comprising a substantially homogenous population of an isolated progeny cell as described above.

In another embodiment, the present invention provides a composition comprising an isolated progeny cell as described above and a pharmaceutically acceptable carrier. In another embodiment, the pharmaceutically acceptable carrier is selected from the group consisting of saline, a gel, a hydrogel, a sponge, and a matrix.

In another embodiment, the present invention provides a tissue-engineering construct comprising an isolated stem cell as described above.

In another embodiment, the present invention provides a tissue-engineering construct comprising the progeny of an isolated stem cell as described above.

In another embodiment, the present invention provides a tissue-engineering construct comprising an isolated stem cell as described above and a progeny cell thereof.

In another embodiment, the present invention provides a method of identifying an agent the induces differentiation of an isolated stem cell as described above comprising contacting said isolated stem cell with a test agent and detecting a change in said isolated stem cell, wherein said change indicates that said agent induces differentiation of said isolated stem cell.

In another embodiment, the present invention provides a method for generating a tissue-engineered construct comprising endothelial cells, said method comprising culturing an isolated stem cell as described above in a tissue-engineered construct.

In another embodiment, the present invention provides a method of treating a vascular disease or disorder comprising administering to a subject in need thereof an isolated stem cell as described above.

In another embodiment, the present invention provides a method of treating a vascular disease or disorder comprising administering to a subject in need thereof an isolated progeny cell as described above.

DETAILED DESCRIPTION OF THE INVENTION

The present invention provides stem cells that can be propagated as stem cells and that can give rise to endothelial and/or endothelial-like cells, methods of isolating and using such stem cells compositions comprising them, and cells derived from them. The stem cells of the invention find utility in gene therapy, tissue engineering, tissue generation, wound repair, diagnostics, as angiogenic agents, as vasculogenic agents, as agents for gene and protein delivery, and as therapeutics.

In one aspect, the present invention provides stem cells comprising characteristics including the ability of self-renewal and differentiation into endothelial and/or endothelial-like cells. In one embodiment, the stem cells of the invention have a doubling time of 18 to 24 hours in monolayer culture and persist for longer periods than primary human endothelial cells known in the art (i.e., HUVECs). The doubling time is dependent upon the number of days the stem cells have been incubated in culture is shorter earlier in culture. In culture, these stem cells adhere and migrate on and/or in collagen-based substrates and are capable of differentiating into cells with typical endothelial cell morphology and/or function.

The stem cells of the present invention express one or more markers associated with an endothelial stem cell phenotype and/or lack one or more markers associated with a differentiated cell (e.g., a cell having a reduced capacity for self-renewal, regeneration, or differentiation) and/or a cell of hematopoietic origin. A molecule is a "marker" of a desired cell type if it is found on a sufficiently high percentage of cells of the desired cell type, and found on a sufficiently low percentage of cells of an undesired cell type, that one can achieve a desired level of purification of the desired cell type from a population of cells comprising both desired and undesired cell types by selecting for cells in the population of cells that have the marker. A marker can be displayed on, for example, 30%, 35%, 40%, 45%, 50%, 55%, 60%, 65%, 70%, 75%, 80%, 85%, 90%, 95%, 99% or more of the desired cell type, and can be displayed on fewer than 50%, 45%, 40%, 35%, 30%, 25%, 20%, 15%, 10%, 5%, 1% or fewer of an undesired cell type. Examples of markers characteristic of a stem cell of the invention include the P1H12 antigen (also known as MUC18 and CD146; Solovey et al., 2001, J. Lab. Clin. Med. 138:322-31; antibodies recognizing same available from, e.g., CRP Inc., Denver, Pa., cat. no. MMS-470R) and AC133 (Bhatia, 2001, Leukemia 15:1685-88). Examples of markers that are typically lacking on stem cells of the invention include CD3, CD14, CD144, CD202b (also known as Tek and Tie-2; see *Leukocyte Typing VII*, Mason et al. (ed.s), Oxford University Press, 2002, pp. 344-46), or any combination thereof.

In one embodiment, the stem cells of the invention, upon isolation, are P1H12$^+$ and AC133$^+$. These stem cells also can be CD34 low or CD34$^-$, CD148$^+$, and/or CD45$^+$ at the time of isolation. The stem cell of the invention also can lack one or more of the phenotypic markers CD14$^-$, CD 144, CD202b, and/or VEGRF2. Accordingly, in another embodiment, the stem cells are P1H12$^+$, CD148$^+$, AC133$^+$, CD34$^+$, CD45$^+$, CD144$^-$, CD202b$^-$, and VEGRF2$^-$.

The term "precursor cell," "progenitor cell," and "stem cell" are used interchangeably in the art and herein and refer either to a pluripotent, or lineage-uncommitted, progenitor cell, which is potentially capable of an unlimited number of mitotic divisions to either renew its line or to produce progeny cells which will differentiate into endothelial cells or endothelial-like cells; or a lineage-committed progenitor cell and its progeny, which is capable of self-renewal and is capable of differentiating into an endothelial cell. Unlike pluripotent stem cells, lineage-committed progenitor cells are generally considered to be incapable of giving rise to numerous cell types that phenotypically differ from each other. Instead, they give rise to one or possibly two lineage-committed cell types.

In one aspect, the present invention provides isolated stem cells, individually or in populations. The term "isolated" or "purified" when referring to stem cells of the invention means cells that are substantially free of cells carrying markers associated with lineage dedication. In particular embodiments, the stem cells are at least 30%, 35%, 40%, 45%, 50%, 55%, 60%, 65%, 70%, 75%, 80%, 85%, 90%, 95% or 99% free of such contaminating cell types. In another embodiment, the isolated stem cells also are substantially free of soluble, naturally occurring molecules. As discussed more fully below, a substantially purified stem cell of the invention can be obtained, for example, by extraction (e.g., via density gradient centrifugation and/or flow cytometry) from a natural source such as a tissue or blood sample. Purity can be measured by any appropriate method. A stem cell of the present invention can be 99%-100% purified by, for example, flow cytometry (e.g., FACS analysis), as discussed below.

In one embodiment, the present invention provides an enriched population of stem cells. An "enriched population of stem cells" is one wherein stem cells of the invention have been partially separated from other cell types, such that the resulting population of stem cells has a greater concentration of stem cells than the original population of cells had. The enriched population of stem cells can have greater than about a 10-fold, 100-fold, 500-fold, 1,000-fold, 2,000-fold, 3,000-fold, 4,000-fold, 5,000-fold, 6,000-fold, 7,000-fold, 8,000-fold, 9,000-fold, 10,000-fold or greater concentration of stem cells than the original population had prior to separation. Stem cells of the invention can, for example, make up at least 5%, 10%, 15%, 20%, 35%, 30%, 35%, 40%, 45%, 50%, 55%, 60%, 65%, 70%, 75%, 80%, 85%, 90%, 95%, 99% or more of the enriched population of stem cells. The enriched population of stem cells may be obtained by, for example, selecting against cells displaying markers associated with differentiated cells, or other undesired cell types, and/or selecting for cells displaying markers associated with the stem cells of the invention, and/or by regenerating isolated stem cells in defined culture systems, as discussed below.

In another embodiment, the present invention provides cell lines of stem cells. As used herein a "cell line" means a culture of stem cells of the present invention, or progeny cells thereof (e.g., endothelial and/or endothelial-like cells), that can be reproduced for an extended period of time, preferably indefinitely, and which term includes, for example, cells that are cultured, cryopreserved and re-cultured following cryopreservation. As used herein a "culture" means a population of endothelial stem cells grown in a medium and optionally passaged accordingly. A stem cell culture may be a primary culture (e.g., a culture that has not been passaged) or may be a secondary or subsequent culture (e.g., a population of cells which have been subcultured or passaged one or more times).

As discussed above, the stem cells of the present invention are characterized by the presence and/or the absence of certain markers that are specifically recognized by a molecule.

Accordingly, in one aspect, the present invention provides methods of labeling stem cells of the invention. In one embodiment, the stem cells are labeled with a molecule (e.g., an antibody) that specifically recognizes a marker that is associated with a stem cell of the invention (e.g., the P1H12 antigen). In another embodiment, a population of cells is contacted with a molecule that specifically binds to a marker under conditions that allow the molecule to bind to the marker, wherein the population of cells comprises at least one stem cell having said marker. In another embodiment, a population of cells is contacted with a molecule that specifically binds to a marker under conditions that allow the molecule to bind to the marker, wherein the population of cells comprises stem cells that do not have the marker and non-stem cells that do have the marker. The molecule used can be, for example, an antibody, an antibody derivative, a ligand, an Fc-peptide fusion molecule (e.g., as described in published PCT application WO 01/83525 A2), or another molecule. The molecule optionally can comprise an additional moiety, for example, one that is detectable (e.g., a fluorescent or colorimetric label) or one that aids in the isolation of the labeled cells (e.g., a moiety that is bound by another molecule or a magnetic particle).

In another aspect, the present invention provides methods of isolating stem cells of the invention. The stem cells of the invention can be isolated by, for example, utilizing molecules (e.g., antibodies, antibody derivatives, ligands or Fc-peptide fusion molecules) that bind to a marker on the stem cells (e.g., the P1H12 antigen, CD34, CD45, AC133, and CD148) and positively selecting cells that bind the molecule (i.e., a positive selection). Other examples of positive selection methods include methods of preferentially promoting the growth of a desired cell type in a mixed population of desired and undesired cell types. Alternatively, by using molecules that bind to markers that are not present on the desired cell type, but that are present on an undesired cell type, the undesired cells containing such markers can be removed from the desired cells (i.e., a negative selection). Other negative selection methods include preferentially killing or inhibiting the growth of an undesired cell type in a mixed population of desired and undesired cell types. Accordingly, by using negative selection, positive selection, or a combination thereof, an enriched population of stem cell can be made.

The endothelial stem cells of the invention can be isolated from a sample obtained from a mammalian subject. The subject can be any mammal (e.g., bovine, ovine, porcine, canine, feline, equine, primate), but is preferably a human. The sample of cells may be obtained from any of a number of different sources including, for example, bone marrow, fetal tissue (e.g., fetal liver tissue), peripheral blood, umbilical cord blood, and the like. Preferably the cell source is peripheral blood due to the use of less invasive techniques to obtain the cellular sample and the readily available donor population.

In order to obtain stem cells of the invention, it is necessary to isolate, separate, or remove the stem cells of the invention from the other cells with which they are normally present. For example, where the source of cells is from peripheral blood the stem cells must be separated or enriched from other cells (e.g., erythrocytes, platelets, monocytes, neutrophils, macrophages, and the like).

Various techniques may be employed to separate the stem cells of the invention by initially removing the stem cells of the invention from other cell types via marker expression characteristics and/or by removing cells of dedicated lineage from the stem cells of the invention in a similar manner. Antibodies (e.g., monoclonal antibodies) are particularly useful for identifying cell surface protein markers associated with particular cell lineages and/or stages of differentiation. The antibodies may be attached to a solid support (e.g., antibody-coated magnetic beads). Examples of commercially available antibodies that recognize lineage dependent markers include anti-AC133 (Miltenyi Biotec, Auburn, Calif.); anti-CD34 (Becton Dickinson, San Jose, Calif.), anti-CD31, anti-CD62E, anti-CD104, anti-CD106, anti-CD1a, anti-CD14 (all available from Pharmingen, Hamburg, Germany); anti-CD144 and anti-CD-13 (Immunotech, Marseille, France). The clone P1H12 (Chemicon, Temecula, Calif.; Catalog Number MAB16985), produces an antibody that specifically reacts with P1H12 antigen (also known as CD146, MCAM, and MUC18). The P1H12 antibody specifically localizes to endothelial cells of all vessels including microvessels of normal and cancerous tissue. The P1H12 antibody does not stain hematopoietic cells.

Procedures for separation may include magnetic separation, using antibody-coated magnetic beads, affinity chromatography, cytotoxic agents joined to a monoclonal antibody, or such agents used in conjunction with a monoclonal antibody, e.g., complement and cytotoxins, and "panning" with antibody attached to a solid matrix (e.g., plate), or other convenient technique. Techniques providing accurate separation include fluorescence activated cell sorters, which can have varying degrees of sophistication, e.g., a plurality of color channels, low angle and obtuse light scattering detecting channels, and impedance channels. Conveniently, antibodies may be conjugated with markers, such as magnetic beads, which allow for direct separation, biotin, which can be removed with avidin or streptavidin bound to a support, fluorochromes, which can be used with a fluorescence activated cell sorter, or the like, to allow for ease of separation of the particular cell type. Any technique may be employed which is not unduly detrimental to the viability of the stem cells.

In one embodiment, magnetic beads linked to antibodies selective for cell surface markers present on a large numbers of lineage committed cells of the hematopoietic systems (e.g., T-cells, B-cells, (both pre-B and B-cells) and myelomonocytic cells) and/or minor cell populations (e.g., megakaryocytes, mast cells, eosinophils and basophils) are used either prior to, simultaneously with, or subsequent to using a P1H12 antigen selection to remove lineage committed cells or other cells from the stem cells of the invention. At least about 30%, 35%, 40%, 45%, 50%, 55%, 60%, 65%, 70%, 75%, 80%, 85%, 90%, 95%, 99% or more of total hematopoietic cells will be removed; however, it is not essential to remove every terminally differentiated cell type. Platelets and erythrocytes can be removed (e.g., by density gradient techniques) prior to sorting or separation of the stem cells from the remaining non-platelet, non-erythrocyte cells. Where positive selection is utilized in the protocol, the dedicated cells lacking the positively selected marker will be left behind. However, in one embodiment both positive and negative selection is used, so that in a final positive selection step, the number of dedicated cells present is minimized. One of skill in the art will recognize that due to the lack of proliferative capacity of many cell types in peripheral blood most, if not all, remaining lineage-defined cells after the positive and/or negative selection process will fail to proliferate and/or adhere to a collagen based substrate and be removed during cell passaging techniques. Compositions having greater than about 30%, 35%, 40%, 45%, 50%, 55%, 60%, 65%, 70%, 75%, 80%, 85%, 90%, 95%, 99% or more may be achieved in this manner, where the desired stem cells are identified by being P1H12$^+$, CD 148$^+$, AC133$^+$, CD34$^+$, CD45$^+$, CD144$^-$, CD202b$^-$, and VEGRF2⁻ and being able to self-renew and give rise to fully differentiated endothelial and/or endothelial-like cells.

Combinations of enrichment methods may be used to improve the time or efficiency of purification or enrichment. For example, after an enrichment step to remove cells having markers that are not indicative of the cell type of interest the cells may be further separated or enriched by a fluorescence activated cell sorter (FACS) or other methodology having high specificity. Multi-color analyses may be employed with a FACS. The cells may be separated on the basis of the level of staining for a particular antigen or lack thereof. Fluorochromes may be used to label antibodies specific for a particular antigen. Such fluorochromes include phycobiliproteins, e.g., phycoerythrin and allophycocyanins, fluorescein, Texas red, and the like. While each of the lineages present in a population may be separated in a separate step, typically by a negative selection process, it is preferred that the cell type of interest be separated in one step in a positive selection process. The cells are typically collected in a complete medium (e.g., EGM2, with the defined supplements; Clonetics Corporation)+15% serum. The serum may be xenogenic, autologous, or allogeneic. Other techniques for positive selection may be employed, which permit accurate separation, such as affinity columns, and the like.

Although the particular order of separation is not critical to this invention a preferred order includes a coarse separation (e.g., density gradient centrifugation), followed by a fine separation (e.g., positive selection of a marker associated with stem cells (e.g., the P1H12 antigen)). Typically density gradient separation is followed by positive selection for P1H12⁺ cells that are then cultured to further culture-out the stem cells of the invention.

Any cell type-specific markers can be used to select for or against a particular cell type. Examples of such markers include CD10/19/20 (associated with B-cells), CD3/4/8 (associated with T-cells), CD14/15/33 (associated with myeloid cells), and Thy-1, which is absent on human T-cells. Also, rhodamine 123 can be used to divide CD34⁺ cells into "high" and "low" subsets. See Spangrude, 1990, Proc. Natl. Acad. Sci. 87:7433 for a description of the use of rhodamine 123 with mouse stem cells. In one embodiment, the stem cells of the invention are for the most part P1H12⁺, CD148⁺, AC133⁺, CD144⁻, CD202b⁻, VEGRF2⁻, and are rhodamine low.

Once stem cells have been isolated, they optionally can be propagated in complete medium (e.g., EGM2 containing the commercially available supplements from Clonetics Corp., e.g., IGF, EGF, FGF, and VEGF)+15% FCS, conditioned medium from other cell types, such as stromal cells (e.g., stromal cells obtained from bone marrow, fetal thymus or fetal liver), medium containing growth factors associated with stem cell maintenance, coculturing with stromal cells, or medium comprising maintenance factors supporting the proliferation of stem cells, where the stromal cells may be, for example, allogeneic or xenogeneic. Before being used in coculture, the mixed stromal cell preparations may be freed of hematopoietic cells employing appropriate monoclonal antibodies for removal of the undesired cells, e.g., with antibody-toxin conjugates, antibody and complement, and the like. Alternatively, cloned stromal cell lines may be used where the stromal lines may be allogeneic or xenogeneic. In addition, the stem cells of the invention may be cultured in a bioreactor system.

In another embodiment, the present invention provides methods of establishing and/or maintaining populations of stem cells, or the progeny thereof, as well as mixed populations comprising both stem cells and endothelial-like progeny cells, and the populations of cells so produced. As with the stem cells of the invention, once a culture of endothelial-like cells or a mixed culture of stem cells and endothelial-like cells is established, the population of cells is mitotically expanded in vitro by passage to fresh medium as cell density dictates under conditions conducive to cell proliferation, with or without endothelial formation. Such culturing methods can include, for example, passaging the cells in culture medium lacking IGF, EGF, FGF, VEGF, and/or other growth factor. Cultures comprising endothelial and/or endothelial-like cells and mixed cultures comprising stem cells and endothelial and/or endothelial-like cells can be transferred to fresh medium when sufficient cell density is reached. Although many of the cell types of the present invention do not demonstrate typical contact inhibition-apoptosis, they become quiescent when density is maximum. Thus, in one embodiment, formation of a confluent monolayer of cells is prevented or minimized by, for example, transferring a portion of the cells to a new culture vessel with fresh medium. Such removal or transfer can be done in any culture vessel that has a cellular monolayer exceeding about a density of about $1 \times 10^6$ cells per T75 tissue culture flask. Alternatively, the culture system can be agitated to prevent the cells from sticking.

Once the stem cells of the invention have been established in culture, as described above, they may be maintained or stored in cell "banks" comprising either continuous in vitro cultures of cells requiring regular transfer, or, preferably, cells which have been cryopreserved.

Cryopreservation of stem cells, or other cell of the invention, may be carried out according to known methods, such as those described in Doyle et al., (eds.), 1995, Cell & Tissue Culture: Laboratory Procedures, John Wiley & Sons, Chichester. For example, but not by way of limitation, cells may be suspended in a "freeze medium" such as, for example, culture medium further comprising 15-20% fetal bovine serum (FBS) and 10% dimethylsulfoxide (DMSO), with or without 5-10% glycerol, at a density, for example, of about $4\text{-}10 \times 10^6$ cells/ml. The cells are dispensed into glass or plastic vials which are then sealed and transferred to a freezing chamber of a programmable or passive freezer. The optimal rate of freezing may be determined empirically. For example, a freezing program that gives a change in temperature of −1° C./min through the heat of fusion may be used. Once vials containing the cells have reached −80° C., they are transferred to a liquid nitrogen storage area. Cryopreserved cells can be stored for a period of years, though they should be checked at least every 5 years for maintenance of viability.

The cryopreserved cells of the invention constitute a bank of cells, portions of which can be withdrawn by thawing and then used to produce a stem cell culture comprising stem cells, endothelial and/or endothelial-like cells, or endothelial tissue as needed. Thawing should generally be carried out rapidly, for example, by transferring a vial from liquid nitrogen to a 37° C. water bath. The thawed contents of the vial should be immediately transferred under sterile conditions to a culture vessel containing an appropriate medium such as complete medium (e.g., EGM2 containing IGF, EGF, FGF, and VEGF)+15% FCS. It is advisable that the cells in the culture medium be adjusted to an initial density of about $1\text{-}3 \times 10^5$ cells/ml so that the cells can condition the medium as soon as possible, thereby preventing a protracted lag phase. Once in culture, the cells may be examined daily, for example, with an inverted microscope to detect cell proliferation, and subcultured as soon as they reach an appropriate density.

The stem cells of the invention may be withdrawn from a cell bank as needed, and used for the production of new stem cells, endothelial and/or endothelial-like cells and/or endothelial tissue either in vitro, for example, as a three dimensional endothelial culture, as described below, or in vivo, for example, by direct administration of cells to the site where new endothelial cells or tissue is needed. As described herein, the stem cells of the invention may be used to produce new endothelial tissue for use in a subject where the cells were originally isolated from that subject's own blood or other tissue (i.e., autologous cells). Alternatively, the cells of the invention may be used as ubiquitous donor cells to produce new endothelial tissue for use in any subject (i.e., heterologous cells).

Once established, a culture of stem cells may be used to produce endothelial-like progeny cells and/or endothelial cells capable of producing new endothelial tissue. Differentiation of stem cells to endothelial cells or endothelial-like cells, followed by the production of endothelial tissue therefrom, can be triggered by specific exogenous growth factors or by changing the culture conditions (e.g., the density) of a stem cell culture. Since the cells are naive, they can be used to reconstitute an irradiated subject and/or a subject treated with chemotherapy; or as a source of cells for specific lineages, by providing for their maturation, proliferation and differentiation into one or more selected lineages. Examples of factors that can be used to induce differentiation include erythropoietin, colony stimulating factors, e.g., GM-CSF, G-CSF, or M-CSF, interleukins, e.g., IL-1, -2, -3, -4, -5, -6, -7, -8, and the like, Leukemia Inhibitory Factory (LIF), Steel Factor (Stl), or the like, coculture with cardiac myocytes, or other lineage committed cells types to induce the stem cells into becoming committed to a particular lineage.

In another aspect, the invention provides methods of culturing stem cells to give rise to progeny cells, and the cells so produced. In one embodiment, the progeny cell is P1H12$^+$, CD144$^+$, AC133$^-$, CD202b$^+$, CD45$^-$, VEGFR2$^+$, has a high proliferative capacity compared to HUVECs and MVECs, and contains Weibel-Palade Bodies.

In another embodiment, the stem cells are genetically engineered to express genes for specific types of growth factors such as, for example, TGF-$\beta$, b-FGF, VEGF, FGF-18, and the like for successful and/or improved differentiation to endothelial cells and/or turnover of endothelial production either pre- or post-implantation. Other factors or genes that can be induced in or transferred into the stem cells or stem cell progeny of the invention for therapeutic benefit include, for example, IL17R, TNFR, angiopoietin-1 and -2, TWEAK, TWEAKR, as well as other anti-inflammatories or angiogenic factors known in the art.

It is believed that native endothelial cell (EC) number and/or viability decreases over time. Thus, in certain patient populations, e.g., the elderly, the resident population of ECs that are competent to respond to angiogenic cytokines may be limited. Accordingly, the stem cells of the invention can provide the desired cell population resulting in increased angiogenic activity and tissue repair.

The cells of the invention may be used to treat subjects requiring the repair or replacement of endothelial tissue resulting from disease or trauma, or to provide a cosmetic function, such as to augment facial or other features of the body. Treatment may entail the use of the cells of the invention to produce new endothelial tissue, and the use of the endothelial tissue thus produced, according to any method presently known in the art or to be developed in the future. For example, the cells of the invention may be implanted, injected or otherwise administered directly to the site of tissue damage so that they will produce new endothelial tissue in vivo. In one embodiment, administration includes the administration of genetically modified endothelial stem cells.

In one embodiment, a formulation comprising the cells of the invention is prepared for injection directly to the site where the production of new endothelial tissue is desired. For example, and not by way of limitation, the cells of the invention may be suspended in a hydrogel solution for injection. Alternatively, the hydrogel solution containing the cells may be allowed to harden, for instance in a mold (e.g., a vascular or tubular tissue construct), to form a matrix having cells dispersed therein prior to implantation. Once the matrix has hardened, the cell formations may be cultured so that the cells are mitotically expanded prior to implantation. A hydrogel is an organic polymer (natural or synthetic) which is cross-linked via convalent, ionic, or hydrogen bonds to create a three-dimensional open-lattice structure, which entraps water molecules to form a gel. Examples of materials which can be used to form a hydrogel include polysaccharides such as alginate and salts thereof, polyphosphazines, and polyacrylates, which are cross-linked ionically, or block polymers such as PLURONICS™ or TETRONICS™ (BASF Corp., Mount Olive, N.Y.), polyethylene oxide-polypropylene glycol block copolymers which are cross-linked by temperature or pH, respectively. Methods of synthesis of the hydrogel materials, as well as methods for preparing such hydrogels, are known in the art.

Such cell formulations may further comprise one or more other components, including selected extracellular matrix components, such as one or more types of collagen known in the art, and/or growth factors and drugs. Growth factors which may be usefully incorporated into the cell formulation include one or more tissue growth factors known in the art or to be identified in the future, such as but not limited to any member of the TGF-$\beta$ family, IGF-I and -II, growth hormone, BMPs such as BMP-13, and the like. Alternatively, the cells of the invention may be genetically engineered to express and produce for growth factors such as BMP-13 or TGF-$\beta$. Details on genetic engineering of the cells of the invention are provided below. Drugs that may be usefully incorporated into the cell formulation include, for example, anti-inflammatory compounds, as well as local anesthetics. Other components may also be included in the formulation include, for example, buffers to provide appropriate pH and isotonicity, lubricants, viscous materials to retain the cells at or near the site of administration, (e.g., alginates, agars and plant gums) and other cell types that may produce a desired effect at the site of administration (e.g., enhancement or modification of the formation of endothelial tissue or its physicochemical characteristics, support for the viability of the cells, or inhibition of inflammation or rejection). The cells can be covered by an appropriate wound covering to prevent cells from leaving the site. Such wound coverings are known to those of skill in the art.

Alternatively, the stem cells of the invention may be seeded onto a three-dimensional framework or scaffold and cultured to, allow the cells to grow and fill the matrix or immediately implanted in vivo, where the seeded cells will proliferate on the surface of the framework and form a replacement endothelial tissue in vivo in cooperation with the cells of the subject. Such a framework can be implanted in combination with any one or more growth factors, drugs, additional cell types, or other components described above that stimulate endothelial formation or otherwise enhance or improve the practice of the invention.

The cells of the invention can be used to produce new endothelial tissue in vitro, which can then be implanted, transplanted or otherwise inserted into a site requiring endothelial tissue repair, replacement or augmentation in a subject. In a non-limiting embodiment, the stem cells of the invention are used to produce a three-dimensional tissue construct in vitro, which is then implanted in vivo. As an example of the production of three-dimensional tissue constructs, see U.S. Pat. No. 4,963,489, issued Oct. 16, 1990, to Naughton et al., which is incorporated herein by reference. For example, the endothelial stem cells or endothelial stem cells and endothelial and/or endothelial-like cells of the invention may be inoculated or "seeded" onto a three-dimensional framework or scaffold, and proliferated or grown in vitro to form a living endothelial tissue which can be implanted in vivo.

The three-dimensional framework may be of any material and/or shape that allows cells to attach to it (or can be modified to allow cells to attach to it) and allows cells to grow in more than one layer. A number of different materials may be used to form the matrix, including but not limited to: nylon (polyamides), dacron (polyesters), polystyrene, polypropylene, polyacrylates, polyvinyl compounds (e.g., polyvinylchloride), polycarbonate (PVC), polytetrafluorethylene (PTFE, teflon), thermanox (TPX), nitrocellulose, cotton, polyglycolic acid (PGA), collagen (in the form of sponges, braids, or woven threads, and the like), cat gut sutures, cellulose, gelatin, or other naturally occurring biodegradable materials or synthetic materials, including, for example, a variety of polyhydroxyalkanoates. Any of these materials may be woven into a mesh, for example, to form the three-dimensional framework or scaffold. The pores or spaces in the matrix can be adjusted by one of skill in the art to allow or prevent migration of cells into or through the matrix material.

The three-dimensional framework, matrix, hydrogel, and the like, can be molded into a form suitable for the tissue to be replaced or repaired. For example, where a vascular graft is desired, the three-dimensional framework can be molded in the shape of a tubular structure and seeded with endothelials stem cells of the invention alone or in combination with stromal cells (e.g., fibroblasts) and cultured accordingly. For example, in addition to the cells of the invention, other cells may be added to the three-dimensional framework so as to improve the growth of, or alter, one or more characteristics of the new endothelial tissue formed thereon. Such cells may include, but are not limited to, fibroblasts, pericytes, macrophages, monocytes, plasma cells, mast cells, and adipocytes, among others.

In yet another embodiment, the stem cells of the invention can be used in conjunction with a three-dimensional culture system in a "bioreactor" to produce endothelial tissue constructs which possess critical biochemical, physical and structural properties of native human endothelial tissue by culturing the cells and resulting tissue under environmental conditions which are typically experienced by native endothelial tissue. Thus, the three-dimensional culture system may be maintained under intermittent and periodic pressurization and the cells of the invention provided with an adequate supply of nutrients by convection. Maintaining an adequate supply of nutrients to the cells of the invention throughout a replacement endothelial tissue construct of approximately 2-5 mm thickness is important as the apparent density of the construct increases. Pressure facilitates flow of fluid through the three-dimensional endothelial construct, thereby improving the supply of nutrients and removal of waste from cells embedded in the construct. The bioreactor may include a number of designs. Typically the culture conditions will include placing a physiological stress on the construct containing cells similar to what will be encountered in vivo. For example, the vascular construct may be cultured under conditions that simulate the pressures and shear forces of blood vessels (see, for example, U.S. Pat. No. 6,121,042, which is incorporated herein by reference).

The stem cells, their progeny, and endothelial tissue of the present invention can be used in a variety of applications. These include, but are not limited to, transplantation or implantation of the cells either in unattached form or as attached, for example, to a three-dimensional framework, as described herein. In addition, injection of extracellular matrix prepared from new endothelial tissue produced by the cells of the invention can be administered to a subject or may be used to further culture cells. Such cells, tissues, and extracellular matrix may serve to repair, replace or augment endothelial tissue that has been damaged due to disease or trauma, or that failed to develop normally, or for cosmetic purposes.

The endothelial tissue produced according to the invention can be used to repair or replace damaged or destroyed endothelial tissue, to augment existing endothelial tissue, to introduce new or altered tissue, to modify artificial prostheses, or to join biological tissues or structures. For example, and not by way of limitation, specific embodiments of the invention would include a replacement heart valve prepared with the endothelial stem cells of the invention or their progeny and vascular tissue or graft. In another embodiment, the cells of the invention are administered in combination with angiogenic factors to induce or promote new capillary or vessel formation in a subject. The cells of the invention can be administered prior to, concurrently with, or following injection of the angiogenic factor. In addition, the cells of the invention may be administered immediately adjacent to, at the same site, or remotely from the site of administration of the angiogenic factor. By angiogenic factor is meant a growth factor, protein or agent that promotes or induces angiogenesis in a subject.

In addition, the cells or endothelial tissue of the invention can be used, for example, to screen in vitro for the efficacy and/or cytotoxicity of compounds, allergens, growth/regulatory factors, pharmaceutical compounds, and the like on endothelial stem cells, to elucidate the mechanism of certain diseases by determining changes in the biological activity of the endothelial stem cells (e.g., proliferative capacity, adhesion), to study the mechanism by which drugs and/or growth factors operate to modulate endothelial stem cell biological activity, to diagnose and monitor cancer in a patient, for gene therapy, gene delivery or protein delivery; and to produce biologically active products.

The endothelial stem cells also can be used in the isolation and evaluation of factors associated with the differentiation and maturation of endothelial stem cells. Thus, the stem cells may be used in assays to determine the activity of media, such as conditioned media, evaluate fluids for cell growth activity, involvement with dedication of particular lineages, or the like. Various systems are applicable and can be designed to induced differentiation of the stem cells based upon various physiological stresses. For example, a bioreactor system that can be employed with the cells of the present invention include bioreactors simulating vascular tissue.

The endothelial stem cells, progeny thereof (e.g., differentiated endothelial and/or endothelial-like cells), and endothelial tissues derived therefrom of the invention may be used in vitro to screen a wide variety of agents for effectiveness and cytotoxicity of pharmaceutical agents, growth/regulatory factors, anti-inflammatory agents, and the like. To this end, the cells or tissue cultures of the invention can be maintained in vitro and exposed to the agent to be tested. The activity of a cytotoxic agent can be measured by its ability to damage or kill endothelial stem cells or their progeny in culture. This can be assessed readily by staining techniques. The effect of growth/regulatory factors can be assessed by analyzing the number of living cells in vitro, e.g., by total cell counts, and differential cell counts. This can be accomplished using standard cytological and/or histological techniques, including the use of immunocytochemical techniques employing antibodies that define type-specific cellular antigens. The effect of various drugs on the cells of the invention can be assessed either in a suspension culture or in a three-dimensional system.

The endothelial stem cells, their progeny, and endothelial tissues derived therefrom of the present invention may afford a vehicle for introducing genes and gene products in vivo to assist or improve the results of implantation and/or for use in gene therapies.

Endothelial stem cells which express a gene product of interest, or endothelial tissue produced in vitro therefrom, can be implanted into a subject who is otherwise deficient in that gene product. For example, genes that express products capable of preventing or ameliorating symptoms of various types of vascular diseases or disorders, or that prevent or promote inflammatory disorders are of particular interest. In one embodiment, the cells of the invention are genetically engineered to express an anti-inflammatory gene product that would serve to reduce the risk of failure of implantation or further degenerative change in endothelial tissue due to inflammatory reaction. For example, an endothelial stem cell of the invention can be genetically engineered to express one or more anti-inflammatory gene products including, for example, peptides or polypeptides corresponding to the idiotype of antibodies that neutralize granulocyte-macrophage colony stimulating factor (GM-CSF), TNF, IL-1, IL-2, or other inflammatory cytokines. IL-1 has been shown to decrease the synthesis of proteoglycans and collagens type II, IX, and XI (Tyler et al., 1985, Biochem. J. 227:69-878; Tyler et al., 1988, Coll. Relat. Res. 82:393-405; Goldring et al., 1988, J. Clin. Invest. 82:2026-2037; and Lefebvre et al., 1990, Biophys. Acta. 1052:366-72). TNF also inhibits synthesis of proteoglycans and type II collagen, although it is much less potent than IL-1 (Yaron, I., et al., 1989, Arthritis Rheum. 32:173-80; Ikebe, T., et al., 1988, J. Immunol. 140:827-31; and Saklatvala, J., 1986, Nature 322:547-49). Also, for example, the cells of the invention may be engineered to express the gene encoding the human complement regulatory protein that prevents rejection of a graft by the host. See, for example, McCurry et al., 1995, Nature Medicine 1:423-27. In another embodiment, the endothelial stem cells may be engineered to include a gene or polynucleotides sequence that expresses or causes to be expressed an angiogenic factor.

Genetically altered stem cells are useful to produce both non-therapeutic and therapeutic recombinant proteins in vivo and in vitro. The endothelial stem cells are isolated from a donor (non-human or human) as described above, transfected or transformed with a recombinant polynucleotide in vitro or ex vivo, and transplanted into the recipient or cultured in vitro. The genetically altered endothelial stem cells or progeny produce the desired recombinant protein in vivo or in vitro. The produced protein or molecule may cause a direct or indirect therapeutic effect or produce a diagnostic protein or molecule.

Alternatively, the endothelial stem cells or progeny of the invention may be genetically engineered to express and produce growth factors such as VEGF, FGF, EGF, IGF, as well as therapeutic agents such as TWEAK, TWEAKR, TNFR, other anti-inflammatory agents, or angiogenic agents. For example, the gene or coding sequence for such growth factors or therapeutic agents would be placed in operative association with a regulated promoter so that production of the growth factor or agent in culture can be controlled. The cells of the invention may be genetically engineered to produce other recombinant products beneficial to transplantation such as anti-inflammatory factors, e.g., anti-GM-CSF, anti-TNF, anti-IL-1, anti-IL-2, and the like. Alternatively, the cells may be genetically engineered to "knock out" expression of native gene products that promote inflammation, e.g., GM-CSF, TNF, IL-1, IL-2, or "knock out" expression of MHC in order to lower the risk of rejection. In addition, the cells may be genetically engineered for use in gene therapy to adjust the level of gene activity in a subject to assist or improve the results of the endothelial transplantation. The genetically engineered cells may be screened to select those cell lines that bring about the amelioration of symptoms of rheumatoid disease or inflammatory reactions in vivo, and/or escape immunological surveillance and rejection.

Conventional recombinant DNA techniques are used to introduce the desired polynucleotide into the stem cells or their progeny. The precise method used to introduce a polynucleotide (e.g., a replacement gene) is not critical to the invention. For example, physical methods for the introduction of polynucleotides into cells include microinjection and electroporation. Chemical methods such as coprecipitation with calcium phosphate and incorporation of polynucleotides into liposomes are also standard methods of introducing polynucleotides into mammalian cells. For example, DNA or RNA can be introduced using standard vectors, such as those derived from murine and avian retroviruses (see, e.g., Gluzman et al., 1988, Viral Vectors, Cold Spring Harbor Laboratory, Cold Spring Harbor, N.Y.). Standard recombinant molecular biology methods are well known in the art (see, e.g., Ausubel et al., 1989, Current Protocols in Molecular Biology, John Wiley & Sons, New York), and viral vectors for gene therapy have been developed and successfully used clinically (Rosenberg, et al., 1990, N. Engl. J. Med, 323:370). Other methods, such as naked polynucleotide uptake from a matrix coated with DNA are also encompassed by the invention (see, for example, U.S. Pat. No. 5,962,427, which is incorporated herein by reference). Examples of proteins, polynucleotides or molecules which can be produced by recombinant stem cells of the invention include GMCSF, IGF, EGF, VEGF, FGF, and the like.

In a further embodiment, the endothelial stem cells of the invention can be cultured in vitro to produce biological products in high yield. For example, such cells, which either naturally produce a particular biological product of interest (e.g., a growth factor, regulatory factor, or peptide hormone and the like), or have been genetically engineered to produce a biological product, could be clonally expanded. If the cells secrete the biological product into the nutrient medium, the product can be readily isolated from the spent or conditioned medium using standard separation techniques, e.g., such as differential protein precipitation, ion-exchange chromatography, gel filtration chromatography, electrophoresis, and HPLC, to name but a few. Alternatively, a biological product of interest may remain within the cell and, thus, its collection may require that the cells are lysed. The biological product may then be purified using any one or more of the above-listed techniques.

Therapeutic uses of the stem cells of the invention include transplanting the stem cells, stem cell populations, or progeny thereof into individuals to treat a variety of pathological states including diseases and disorders resulting from myocardial damage, circulatory or vascular disorders or diseases, as well as tissue regeneration and repair. Stem cells or stem cell populations (including genetically altered stem cells) are introduced into a subject in need of such stem cells or in need of the protein or molecule encoded or produced by the genetically altered cell. For example, in one embodiment, the stem cells can be administered to cancer patients who have undergone chemotherapy that have killed, reduced, or damaged endothelial stem cells, endothelial cells, or endothelium of a subject.

If the stem cells are derived from heterologous source compared to the recipient subject, concomitant immunosuppression therapy is typically administered, e.g., administration of the immunosuppressive agent cyclosporine or FK506. However, due to the immature state of the stem cells of the invention such immunosuppressive therapy may not be required. Accordingly, in one embodiment, the stem cells of the invention can be administered to a recipient in the absence of immunomodulatory (e.g., immunsuppressive) therapy. Alternatively, the cells can be encapsulated in a membrane, which permits exchange of fluids but prevents cell/cell contact. Transplantation of microencapsulated cells is known in the art, e.g., Balladur et al., 1995, Surgery 117:189-94, 1995; and Dixit et al., 1992, Cell Transplantation 1:275-79.

The cells may be introduced directly into the peripheral blood or deposited within other locations throughout the body, e.g., the spleen, pancreas, or on microcarrier beads in the peritoneum. For example, $10^2$ to $10^9$ cells can be transplanted in a single procedure, and additional transplants can be performed as required.

Differentiation of the stem cells can be induced ex vivo, or alternatively may be induced by contact with tissue in vivo, (e.g., by contact with endothelial cells or cell matrix components). Optionally, a differentiating agent may be co-administered or subsequently administered to the subject to promote stem cell differentiation.

Unless otherwise defined, all technical and scientific terms used herein have the same meaning as commonly understood by one of ordinary skill in the art to which this invention belongs. All headings and subheading provided herein are solely for ease of reading and should not be construed to limit the invention. The terms "a", "an" and "the" as used herein are meant to encompass the plural unless the context clearly dictates the singular form. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. The following examples are intended to illustrate particular embodiments and not to limit the scope of the invention.

EXAMPLES

Example 1

Endothelial Stem Cell Isolation

A volume of 200 cc of sodium heparinized human blood was fractionated by centrifugation over FICOLL™ (Amersham Biosciences, Piscataway, N.J.) having a specific gravity of 1.077 to isolate PBMC. The isolated PBMCs present in the "buffy coat" were resuspended at approximately, and not more than, $100\times10^6$ cell/ml in complete medium (EGM2 containing IGF, FGF, EGF, and VEGF+15% FCS; Cambrex Bioscience, Inc., Baltimore, Md.). Ten µg/ml of mouse anti-P1H12 antibodies (Chemicon MAB16985) were added to the cells and incubated for 1 hr at room temperature.

The cells were washed two times in complete medium or phosphate buffered saline (PBS) and resuspended at approximately, but not more than, $100\times10^6$ cells in 1 ml of PBS. Twenty µl of magnetic anti-muIgG-MACS filings (cat. no. 130-047-101, Miltenyi Biotec, Auburn, Calif.) were added to 20 µl containing about $10\times10^6$ cells to antibody label the cells, and the cells were incubated at 4° C. for 15 minutes. The antibody labeled cells were washed once in PBS+3% bovine serum albumin (BSA), and resuspended in a final volume of 5 ml PBS+3% BSA.

The antibody labeled cells were then run over a prepped MACS LS column on a VARIOMAC™ magnet (Miltenyi Biotec). The flow-through fraction was collected and discarded, and the column was washed three times with PBS+3% BSA. The labeled cells were removed from the column by washing the column in the absence of the magnetic field. The eluted fraction was washed and counted.

Positive fraction cells were cultured at approximately, but typically not more than, $1-5\times10^6$ cells per well of a 6 well collagen IV plate (Becton Dickinson, Franklin Lakes, N.J.) in complete medium. After 48 hours, non-adherent cells were removed. The medium was dermidepleted twice a week.

Example 2

Endothelial Stem Cell Characterization

Cells were characterized by FACS at isolation and at various time points as indicated in the Tables below.

At isolation the cells appeared to express relatively high levels of P1H12 antigen, CD148, and AC133. Cells were negative for CD202b and CD144. In some isolates a subpopulation of CD45+ cells also expressed CD34+. The amount of these CD45+/CD34+ double positive cells expressed as a percentage of total cells varied and in some instances was 100%. Table 1 shows the measured markers present on the cells at the time of isolation. Mouse IgG1 was used as a control for flow cytometry; the control data are presented in Table 1.

TABLE 1

Flow Cytometry Analysis and Phenotype of Cells after Enrichment for P1H12+ cells

| surface markers | donor 46 | donor 526 | donor 55 | donor 374 | donor 119b | donor 301 | donor 512 | donor 143 | donor 546 |
|---|---|---|---|---|---|---|---|---|---|
| day of assay | d0 | d0 | d0 | d0 | d0 | d0 | d0 | d0 | d0 |
| control | 3.6 | 6.93 | 8.54 | 7.96 | 3.97 | 2.32 | 3.27 | 2.3 | 3.05 |
| P1H12 | 23.43 | 50.2 | 53.99 | 31.71 | 44.81 | 88.18 | 20.58 | 28.77 | 17.97 |
| CD148 | ND | 76.17 | 93.08 | 37.23 | 88.76 | 51.99 | ND | ND | ND |
| CD144 | ND | 20.34 | 36.35 | 3.5 | 18.06 | 2.4 | 4.43 | 3.9 | 1.78 |
| AC133 | ND | 89.79 | 96.01 | 73.01 | 92.23 | 95.44 | 33.71 | 66 | 33 |
| CD45 | 98.56 | 98.61 | 93.02 | 95.16 | 99.24 | 94 | 97.08 | 96.3 | 96.3 |
| CD34 | ND | 0.86 | 1.51 | 4.72 | ND | 50.02 | 1.4 | 96.3 | 1.96 |
| CD202b | ND | 7.65 | 12.23 | 0.16 | 7.26 | 0.87 | 3.31 | 0.56 | 0.59 |
| CD45/CD34 double pos | ND | 0.86 | 1.51 | 4.72? | 99.24 | 50.02 | 1.4 | 96.3 | 1.96 |
| aVEGFR2 | ND | ND | ND | ND | ND | ND | 9.63 | 1.6 | 0.79 |
| P1H12/AC133 double pos | ND | ND | ND | ND | ND | ND | 16.42 | 54.25 | 28.49 |
| CD34/AC133 double pos | ND | ND | ND | ND | ND | ND | 8.92 | 30.06 | 47.96 |

During culture the appearance of the endothelial stem cells changed and the markers present on the cells changed as shown in Table 2.

TABLE 2

Summary of Surface Markers for a Single Donor over time

| DONOR #46 | initial isolation | just before transition Day 14 | during transition Day 22 | Passage 5 Day 35 | Passage 7 Day 45 | Passage 12 Day 59 |
|---|---|---|---|---|---|---|
| control | 3.6 | 6.9 | 9.31 | 6.26 | 9.93 | 5.27 |
| P1H12 | 23.43 | 33.28 | 97.85 | 75.06 | 99.27 | 91.44 |
| CD148 | ND | 97.53 | 51.31 | 87.74 | 92.66 | 91.93 |
| CD144 | ND | 8.48 | 98.96 | 83.88 | 66.85 | 89.05 |
| AC133 | ND | ND | 20.15 | 8.56 | 31.56 | ND |
| CD45 | 98.56 | 16.45 | 2.8 | 0.56 | 0.45 | 0.25 |
| CD34 | ND | 0 | 70.44 | 3.56 | 2.14 | 16.06 |
| CD202b | ND | 2.07 | 97.25 | 95.07 | 88.44 | 94.09 |
| CD45/CD34 double pos | ND | 83.5 | 7.77 | 1.44 | 0.54 | 2.28 |

Example 3

Figure 1:
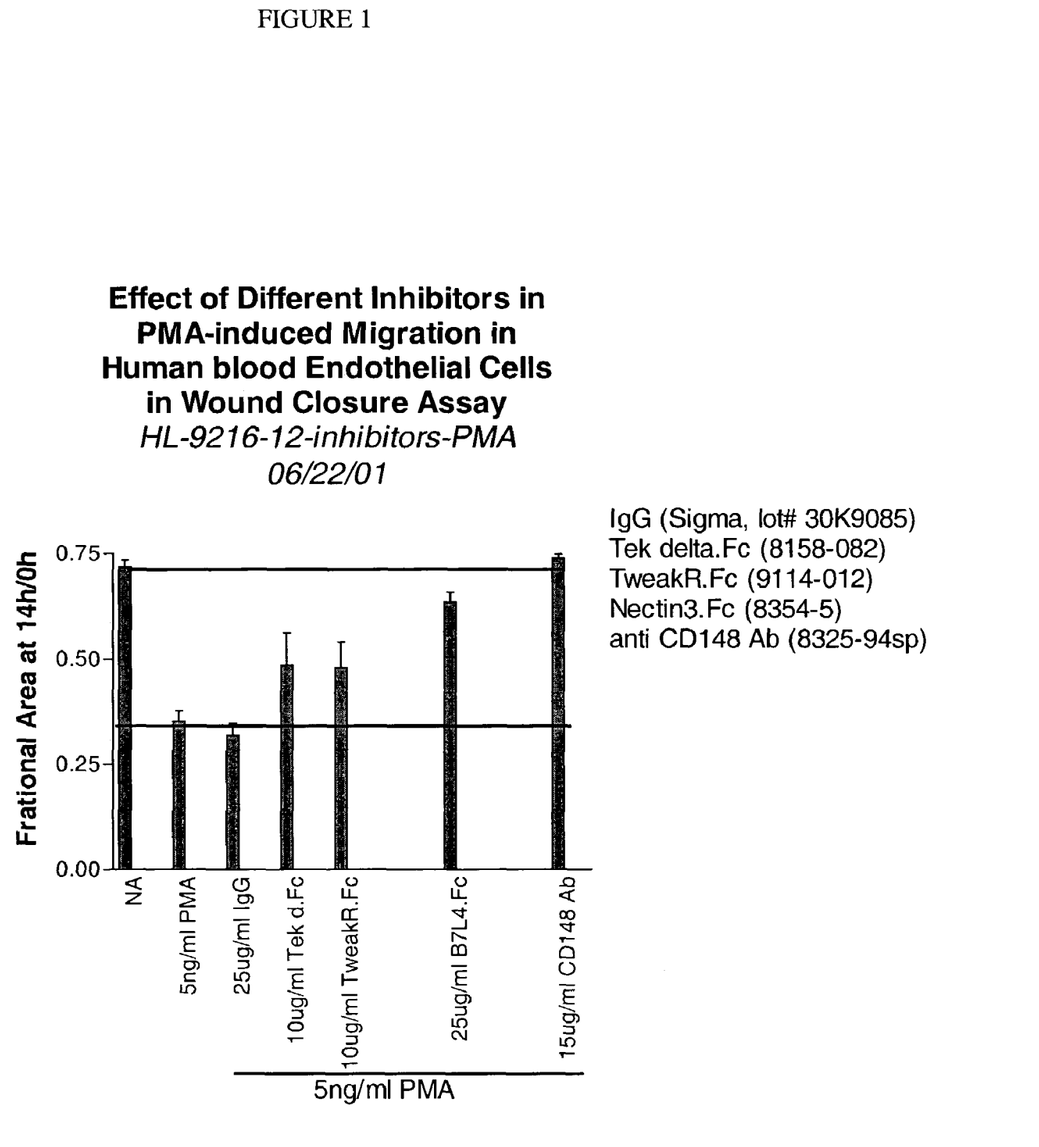
FIG. 1 shows the effect of different inhibitors in PMA-induced migration of stem cell derived human blood endothelial cells in a wound closure assay.
Figure 2:
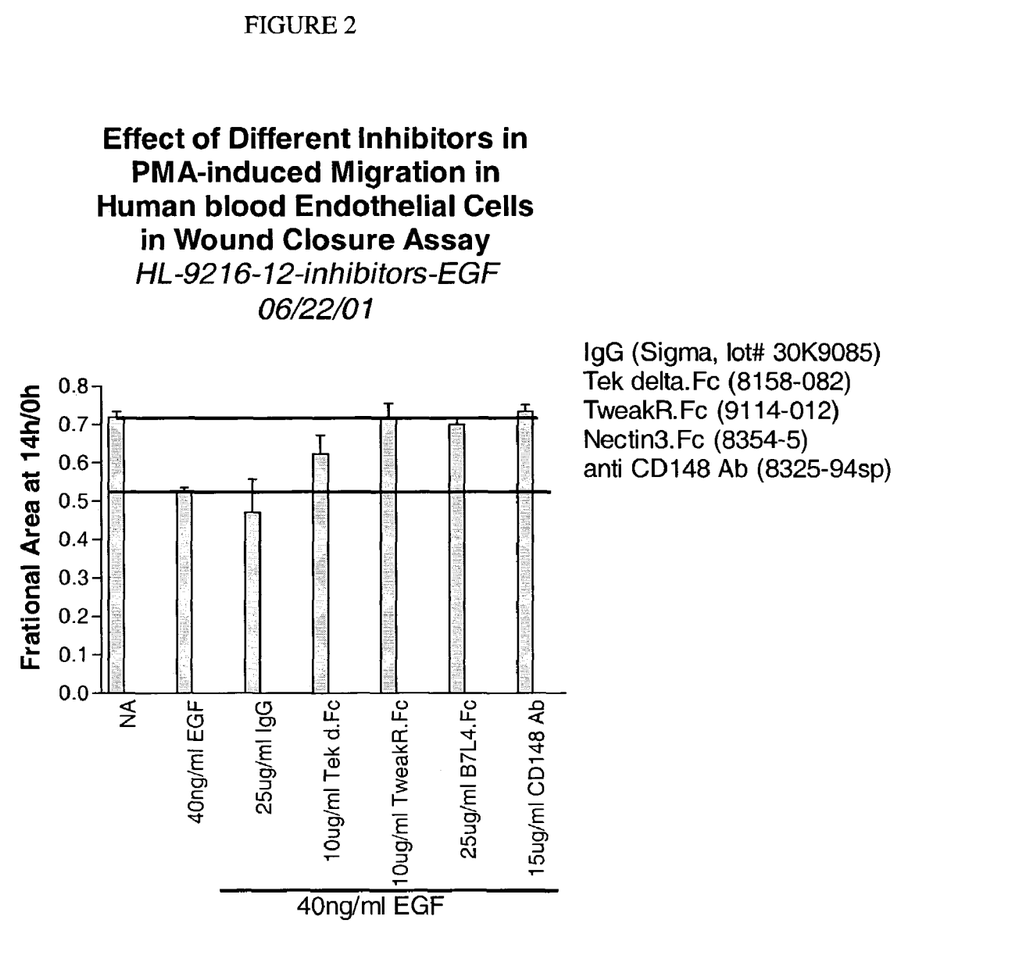
FIG. 2 shows the effect of different inhibitors in EGF-induced migration of stem cell derived human blood endothelial cells in a wound closure assay.
Figure 3:
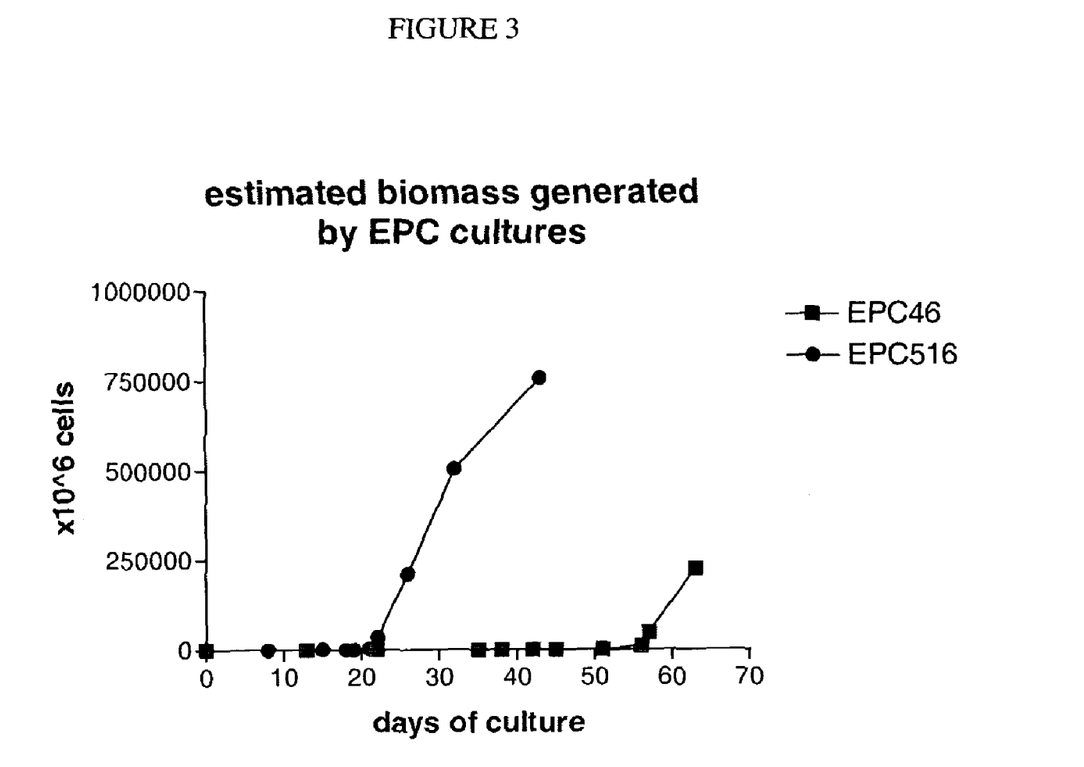
FIG. 3 shows the proliferative capacity of the stem cells and progeny cells of the invention expressed as the production of biomass.

Planar Migration of Human Peripheral Blood Stem Cell-Derived Endothelial Cells in Response to Stimulus and the Effect of Migration Inhibitors A planar endothelial cell migration (wound closure) assay was used to quantify the migration of human peripheral blood-derived endothelial cells in response to PMA, EGF and other migration stimuli. In this assay, endothelial cell migration is measured as the rate of closure of a circular wound in a cultured cell monolayer. The rate of wound closure is linear in renal and skin microvascular endothlelial cells, and is dynamically regulated by agents that stimulate and inhibit angiogenesis in vivo. Both renal microvascular endothelial cells and dermal microvascular cells migrate in response to PMA and EGF and this migration can be regulated by the addition of antiangiogenic agents to the migration culture (Wiley et al., 2001, Immunity 15: 837-46). Peripheral blood human stem cells were isolated as described herein and their progeny of primary human peripheral blood-derived endothelial cells, hPBEC, were isolated, cultured, and used between passage 6-11 as described herein. Replicate circular lesions, "wounds" (600-800 micron diameter), were generated in overnight serum starved (DMEM+0.5% FBS) confluent hPBEC monolayers at about 80,000 cells/well using a silicon-tipped drill press. At the time of wounding the medium (DMEM+0.1% FBS) was supplemented with 5 ng/ml PMA (phorbol-12-myristate-13-acetate), 40 ng/ml EGF or combinations of 5 ng/ml PMA or EGF and migration inhibitors. The residual wound area was measured as a function of time (0-14 hours) using a microscope and image analysis software (Bioquant; Nashville, Tenn.). The relative migration rate was calculated for each agent and combination of agents by linear regression of residual wound area plotted over time. The results are shown in FIG. 1-2. The hPBEC migrated well in response to PMA (>=50%) (FIG. 1) and more slowly in response to EGF (>=35% at) (FIG. 2). Addition of the anti-angiogenic agents huTekΔFc (WO 00/75323), TweakR.Fc (WO 01/45730), nectin-3α-Fc (B7L4.Fc) (WO 02/28902), and CD 148 mAb at the concentrations indicated inhibited PMA-induced hPBEC migration 40%, 40%, 70% and 100%, respectively, compared to huIgG control protein (FIG. 1). Addition of the anti-angiogenic agents huTekΔFc, TweakR.Fc, nectin-3α-Fc (B7L4.Fc), and anti-CD148 mAb at the concentrations indicated inhibited EGF-induced hPBEC migration 50%, 100, 95%, and 100%, respectively, compared to huIgG control protein (FIG. 2).

Example 4

Barrier Migration Assay

Endothelial stem cells were cultured overnight (18 hours) in medium (e.g., EGM-2 media, Clonetics, Walkersville, Md.) and in the presence or absence of PMA (50 ng/ml), and then the cells were washed and labeled in PBS containing 4 µM calcein dye for two hours. After calcein labeling the cells were excited to fluoresce by excitation at 488 nm. The cells were washed in PBS, resuspended in basal medium (EBM+/– 0.1% FBS), and placed into culture in 3 micron pore size fluoroblock inserts for 24-well plates. Fifty thousand stem cells including differentiated endothelial cell progeny were cultured in 300 microliters of basal medium in the fluorblock insert and the inserts containing the cells were placed into 24-well sterile culture plates containing 1 ml of medium with cytokines and/or serum having the potential to cause migration or movement (haptotaxis) of the cells of the invention through the opaque 3 micron filter of the insert into the 24-well plate. Migration of cells through the filter was detected by measuring the level of fluorescence emission observed at 530 nm in the bottom well using a multilabel counter. The migration results were similar to the planar migration assay results of Example 3, above.

Example 5

Capillary Tube/Chord Formation Assay

MATRIGEL™ matrix (Becton Dickinson, Bedford, Mass.), a solubilized basement membrane preparation extracted from the Engelbreth-Holm-Swarm (EHS) mouse sarcoma, was thawed overnight at 4° C. on ice. A 24 well plate (BD Labware, Franklin Lakes, N.J.) and 1000 µl pipette tips were also chilled overnight at 4° C. On the day of assay, the plate wells were evenly coated with 300 µl of MATRIGEL™ per well, taking care not to introduce bubbles. The coated plates were allowed to incubate at 37° C. for 30 minutes to allow the matrix to polymerize.

Endothelial stem cells and/or endothelial cells derived from the stem cells were trypsinized, washed in fresh complete medium (as described in Example 1), and counted. Thirty-thousand cells per well were plated in 100 µl growth medium and incubated at 37° C. for 30 minutes. Five hundred microliters of fresh growth medium was added.

The cells were observed at 4 and 5 hours after plating. Control cells treated identically except for plating on MATRIGEL™ were used for comparison. At 4 hours control cells showed general scattered adherence characteristic of cells grown tissue culture plastic. Cells grown on MATRIGEL™ for 4 hours formed multiple foci with cells connecting the foci giving the appearance of lumenal chords. The appearance of abundant lumenal structures was clear by observation by 24 hours in culture.

Example 6

In vivo Localization of Administered Stem Cell and Stem Cell Progeny

This example demonstrates that cells isolated by the method described herein migrate in vivo to areas having angiogenic and/or vasculogenic activity.

Donor 1017 human peripheral blood derived endothelial cells (hPBEC; expanded from blood derived endothelial progenitor cells as described in Example 3) were labeled in vitro with one micron fluorescent green yellow beads (emission at 515 nM; Molecular Probes, Eugene, Oreg.). Cell labeling was accomplished by incubation of donor 1017 hPBEC ($5 \times 10^6$ beads per $1 \times 10^6$ cells) for 18 hours. Adherent cells that had incorporated beads were removed with brief trypsinization and washed once in PBS, to remove unincorporated beads, and replated in EC growth medium (as described in Example 1) and allowed to reattach. Cell labeling was confirmed by inverted light microscopy and immunofluorescence. On the day of injection (see below), the labeled 1017 hPBEC were removed by brief trypsinization and resuspended in PBS for intradermal (i.d.) or intravenous (i.v.) injection. Labeled human dermal microvascular endothelial cells (hMVEC-d) served as a control and $5 \times 10^6$ fluorescent beads alone administered i.d served as a negative control.

Less than 24 hr old neonatal BALB/c hearts were transplanted into the ear pinnae (bilateral) of anaesthetized twelve week old female BALB/c SCID mice (Jackson Labs, Bar Harbor, Me.). Immediately following transplantation, the mice were injected in the ear, 4-5 mm from the transplanted heart, with either labeled donor 1017 hPBEC cells ($1 \times 10^6$ cells, i.d. or $2 \times 10^6$ cells, i.v.), fluorescent beads only ($5 \times 10^6$ beads, i.d.) or labeled hMVEC-d cells ($1 \times 10^6$ cells).

Immediately after i.d injection of cells, the ear of the anaesthetized mouse was imaged using a microscope system comprising a motorized inverted microscope fitted with 4× and 10× objectives and a CCD camera to detect low light fluorescence, controlled by OPENLAB™ software (Improvision, Inc., Lexington, Mass.)) to confirm the deposit of green immunofluorescent cells at the injection site. The ear isografts were imaged in each recipient mouse at both 24 hr and 144 hours post transplant/cell injection.

Deposits of both living labeled hPBEC (donor 1017) or fluorescent beads alone were observed confined to the injection site immediately (1-2 hours) after injection. By 24 hr post injection, labeled hPBEC could be observed migrating away from the injection site towards the ischemic heart. By 144 hr post injection, the heart isografts were pulsatile and a greater number of the labeled, i.d. injected hPBEC had migrated from the injection site toward the heart isograft. Some hPBEC had migrated into the portion of the beating heart isograft where neovascularization occurs, or into the area immediately adjacent to it. Neither i.d. injected beads nor i.v. injected labeled cells could be detected 24 hr or 144 hr post-injection. The i.d. injected cells were localized to the interdermal space, near the exposed skin surface, allowing the imaging device to more readily track them than i.v. injected cells, which needed to be tracked histologically.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of enriching P1H12+ CD45+ endothelial stem cells, comprising the steps of:
    a. contacting isolated, uncultured peripheral blood mononuclear cells (PBMC) comprising said P1H12+ CD45+ endothelial stem cells with an antibody specific for P1H12 under conditions that allow said antibody to bind to said P1H12+ CD45+ endothelial stem cells, and
    b. separating cells bound to said antibody from PBMC cells not bound to said antibody.

2. The method of claim 1, wherein said enriched P1H12+ CD45+ endothelial stem cells are also enriched for one or more of the markers selected from the group consisting of CD148, AC133, and CD34.

3. An isolated P1H12+ CD45+ endothelial stem cell.

4. The isolated P1H12+ CD45+ endothelial stem cell of claim 3, wherein said cell is positive for one or more of a marker selected from the group consisting of CD148, AC133, and CD34.

* * * * *